United States Patent
Nesterenko et al.

(10) Patent No.: US 9,260,356 B2
(45) Date of Patent: *Feb. 16, 2016

(54) METHOD FOR MAKING A CATALYST COMPRISING A PHOSPHORUS MODIFIED ZEOLITE TO BE USED IN A MTO PROCESS

(71) Applicant: TOTAL RESEARCH & TECHNOLOGY FELUY, Seneffe (Feluy) (BE)

(72) Inventors: Nikolai Nesterenko, Nivelles (BE); Sander Van Donk, Sainte-Adresse (FR); Delphine Minoux, Nivelles (BE); Jean-Pierre Dath, Beloeil (BE)

(73) Assignee: Total Research & Technology Feluy, Feluy (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/592,756

(22) Filed: Jan. 8, 2015

(65) Prior Publication Data
US 2015/0148579 A1    May 28, 2015

Related U.S. Application Data

(63) Continuation of application No. 13/522,623, filed as application No. PCT/EP2011/050963 on Jan. 25, 2011, now Pat. No. 8,981,173.

(30) Foreign Application Priority Data

Jan. 25, 2010   (EP) ..................................... 10151507

(51) Int. Cl.
| | |
|---|---|
| C07C 1/24 | (2006.01) |
| B01J 29/06 | (2006.01) |
| B01J 29/40 | (2006.01) |
| B01J 37/00 | (2006.01) |
| B01J 37/28 | (2006.01) |
| C07C 1/20 | (2006.01) |
| B01J 29/85 | (2006.01) |
| B01J 37/06 | (2006.01) |
| B01J 37/08 | (2006.01) |
| B01J 27/16 | (2006.01) |

(52) U.S. Cl.
CPC . *C07C 1/24* (2013.01); *B01J 29/06* (2013.01); *B01J 29/40* (2013.01); *B01J 29/85* (2013.01); *B01J 37/0009* (2013.01); *B01J 37/0045* (2013.01); *B01J 37/06* (2013.01); *B01J 37/08* (2013.01); *B01J 37/28* (2013.01); *C07C 1/20* (2013.01); *B01J 27/16* (2013.01); *B01J 2229/18* (2013.01); *B01J 2229/36* (2013.01); *B01J 2229/37* (2013.01); *B01J 2229/42* (2013.01); *C07C 2529/40* (2013.01); *C07C 2529/85* (2013.01)

(58) Field of Classification Search
USPC .............. 585/639, 640, 641, 642; 502/60, 77, 502/121, 150, 155, 162, 208
See application file for complete search history.

(56) References Cited

U.S. PATENT DOCUMENTS

| | | | | |
|---|---|---|---|---|
| 5,367,100 A | * | 11/1994 | Gongwei et al. | ............... 585/640 |
| 6,797,851 B2 | * | 9/2004 | Martens et al. | ............... 585/640 |

FOREIGN PATENT DOCUMENTS

EA           201270694 A1    12/2012

OTHER PUBLICATIONS

Ouyang et al. Catalytic Conversion of Bio-Ethanol to Ethylene over La-Modified HZSM-5 Catalysts in a Bioreactor. 2009, Cataly Letter 132:64-74.*
Atlas of Zeolite Structure Types, 1987, Butterworths.
Office Action issued in Eurasian Application No. 201270686/28, dated Aug. 14, 2014, 2 pages.

* cited by examiner

*Primary Examiner* — In Suk Bullock
*Assistant Examiner* — Sharon Pregler
(74) *Attorney, Agent, or Firm* — Albert Shung

(57) ABSTRACT

The present invention is the use of a catalyst in a MTO process to convert an alcohol or an ether into light olefins wherein said catalyst comprises a phosphorus modified zeolite and is made by a method comprising the following steps in this order,
a) the essential portion of the phosphorus is introduced into a zeolite comprising at least one ten members ring in the structure,
b) the phosphorus modified zeolite of step a) is mixed with at least a component selected among one or more binders, salts of alkali-earth metals, salts of rare-earth metals, clays and shaping additives,
b)* making a catalyst body from mixture b),
c) an optional drying step or an optional drying step followed by a washing step,
d) a calcination step,
d*) an optional washing step followed by drying,
e) optionally a small portion of phosphorus is introduced in the course of step b) or b)* or at end of step b) or b)*.

24 Claims, No Drawings

METHOD FOR MAKING A CATALYST COMPRISING A PHOSPHORUS MODIFIED ZEOLITE TO BE USED IN A MTO PROCESS

CROSS-REFERENCE TO RELATED APPLICATIONS

This application is a continuation of U.S. patent application Ser. No. 13/522,623, filed on Oct. 8, 2012, which is a national stage entry of PCT/EP2011/050963, filed on Feb. 25, 2011, which claims priority from EP 10151507.0, filed on Jan. 25, 2010.

FIELD OF THE INVENTION

The present invention relates to a method for making a catalyst comprising a phosphorus modified zeolite to be used in a MTO process. More precisely it relates to the use of a catalyst in a MTO process to convert an alcohol or an ether into light olefins wherein said catalyst comprises a phosphorus modified zeolite. Olefins are traditionally produced from petroleum feedstocks by catalytic or steam cracking processes. These cracking processes, especially steam cracking, produce light olefin(s), such as ethylene and/or propylene, from a variety of hydrocarbon feedstock. Ethylene and propylene are important commodity petrochemicals useful in a variety of processes for making plastics and other chemical compounds.

The limited supply and increasing cost of crude oil has prompted the search for alternative processes for producing hydrocarbon products. The MTO process produces light olefins such as ethylene and propylene as well as heavy hydrocarbons such as butenes. Said MTO process is the conversion of methanol or dimethylether by contact with a molecular sieve. The interest in the methanol to olefin (MTO) process is based on the fact that methanol can be obtained from coal or natural gas by the production of synthesis gas which is then processed to produce methanol.

BACKGROUND OF THE INVENTION

Catalysts comprising a phosphorus modified zeolite (the phosphorus modified zeolite is also referred as P-zeolite) are known The following prior arts have described various methods to make said catalysts.

US 2006 106270 relates to the use of a dual-function catalyst system in the hydrocarbon synthesis reaction zone of an oxygenate to propylene (OTP) process that operates at relatively high temperatures preferably with a steam diluent and uses moving bed reactor technology. The dual-functional catalyst system comprises a molecular sieve having dual-function capability dispersed in a phosphorus-modified alumina matrix containing labile phosphorus and/or aluminum anions. It is explained that the hydrothermal stabilization effect that is observed when this phosphorus-modified alumina matrix is utilized is caused by migration or dispersion of phosphorus and/or aluminum anions from this matrix into the bound molecular sieve. These anions are then available to repair, anneal and/or stabilize the framework of the molecular sieve against the well-known dealumination mechanism of molecular sieve framework destruction or modification that is induced by exposure to steam at temperatures corresponding to those used in the OTP reaction zone and in the regeneration zone.

U.S. Pat. No. 4,356,338 discloses a method for decreasing catalyst coking and extending the usable catalyst life by pretreatment of the catalyst with steam and/or a phosphorus-containing compound. Pretreatment may be accomplished by the impregnation of the catalyst or of the catalyst/binder combination with a phosphorus containing compound to deposit approximately 4 wt. % of phosphorus thereon, and preferably from about 2% to about 15% by weight of phosphorus, based on the weight of the catalyst or catalyst/binder matrix being treated.

U.S. Pat. No. 5,231,064 is directed to a fluid catalyst comprising clay and a zeolite, at least one of which has been treated with a phosphorus containing compound, for example ammonium dihydrogen phosphate or phosphoric acid, and which is spray dried at a low pH, preferably lower than about 3. Said catalysts are deemed to advantageously exhibit reduced attrition.

EP 511013 A2 provides an improved process for the production of C2-C5 olefins from higher olefinic or paraffinic or mixed olefin and paraffin feedstocks. In accordance with this prior art, the hydrocarbon feed materials are contacted with a particular ZSM-5 catalyst at elevated temperatures, high space velocity and low hydrocarbon partial pressure to produce lower olefins. The catalysts is treated with steam prior to use in the hydrocarbon conversion. The active catalyst component is phosphorus-containing ZSM-5 having a surface Si/Al ratio in the range 20-60. Preferably, the phosphorus is added to the formed ZSM-5 as by impregnating the ZSM-5 with a phosphorus compound in accordance with the procedures described, for example, in U.S. Pat. No. 3,972,832. Less preferably, the phosphorus compound can be added to the multicomponent mixture from which the catalyst is formed. The phosphorus compound is added in amount sufficient to provide a final ZSM-5 composition having 0.1-10 wt. % phosphorus, preferably 1-3 wt. %.

The phosphorus-containing ZSM-5 is preferably combined with known binders or matrices such as silica, kaolin, calcium bentonite, alumina, silica aluminate and the like. The ZSM-5 generally comprises 1-50 wt. % of the catalyst composition, preferably 5-30 wt. % and most preferably 10-25 wt. %.

EP 568913 A2 describes a method for preparing a ZSM-5 based catalyst adapted to be used in the catalytic conversion of methanol or dimethyl ether to light olefins, wherein it comprises the following consecutive steps:
mixing a zeolite ZSM-5 based catalyst with silica sol and ammonium nitrate solution,
kneading, moulding, drying and calcining the mixture,
exchanging the modified zeolite with a solution of HCl at 70-90° C.,
drying and calcining the H-modified zeolite,
impregnating the H-modified zeolite with phosphoric acid under reduced pressure,
drying and calcining the P-modified zeolite,
impregnating the P-modified zeolite with a solution of rare earth elements under reduced pressure,
drying and calcining the P-rare earths-modified zeolite,
hydrothermally treating the P-rare earths-modified zeolite at 500-600° C. with water vapour, and
calcining the modified zeolite.

WO 03 020667 relates to a process of making olefin, particularly ethylene and propylene, from an oxygenate feed, comprising contacting an oxygenate feed with at least two different zeolite catalysts to form an olefin composition, wherein a first of the zeolite catalysts contains a ZSM-5 molecular sieve and a second of the zeolite catalysts contains a zeolite molecular sieve selected from the group consisting of ZSM-22, ZSM-23, ZSM-35, ZSM-48, and mixtures thereof. The ZSM-5 can be unmodified, phosphorous modified, steam modified having a micropore volume reduced to not less than 50% of that of the unsteamed ZSM-5, or various mixtures thereof. According to one embodiment, the zeolite is modified with a phosphorous containing compound to control reduction in pore volume. Alternatively, the zeolite is steamed, and the phosphorous compound is added prior to or after steaming. The amount of phosphorous, as measured on an elemental basis, is from 0.05 wt. % to 20 wt. %, and preferably is from 1 wt. % to 10 wt. %, based on the weight of the zeolite molecular sieve. Preferably, the atomic ratio of phosphorus to framework aluminum (i.e. in the zeolite framework) is not greater than 4:1 and more preferably from 2:1 to 4:1. Incorporation of a phosphorus modifier into the catalyst of the invention is accomplished, according to one embodiment, by contacting the zeolite molecular sieve either alone or the zeolite in combination with a binder with a solution of an appropriate phosphorus compound. The solid zeolite or zeolite catalyst is separated from the phosphorous solution, dried and calcined. In some cases, the added phosphorous is converted to its oxide form under such conditions. Contact with the phosphorus-containing compound is generally conducted at a temperature from 25° C. to 125° C. for a time from 15 minutes to 20 hours. The concentration of the phosphorus in the zeolite may be from 0.01 wt. % to 30 wt. %. This prior art discloses a non-formulated P-ZSM-5.

A common way to produce a formulated P-zeolite containing catalyst consists in the impregnation of the already preformulated zeolite (e.g. the zeolite+a binder) with P-compounds or phosphorous addition to the reaction medium.

A great number of patents disclose the recipe for preparation of the active phase (non-formulated phosphated zeolite) by means of zeolite phosphatation and their use in methanol conversion. Some of these references contain the options of further blending the active phase with binder. However, the active phase is good as such in the reaction. It is assumed that the binder plays only the role of diluent what is not normally the case. The process of the present invention differs from a great number of known in the art preparation of the P-zeolite based active phase due to referring to preparation of formulated catalyst and implementation of the phosphatation step at the first stage. Moreover the phosphatation of the zeolite (formation of the active phase) at the first step does not necessarily leads to a suitable catalyst. On the contrary, the overall recipe results in a good catalyst.

The catalyst referred to in the present invention comprises a zeolite and at least a component selected among one or more binders, salts of alkali-earth metals, salts of rare-earth metals, clays and shaping additives. The metal salts, binder and clays may also adsorb the phosphorous interfering and even competing with zeolite preventing a proper zelolite phosphatation. The presence of traces of metals adsorbing preferentially phosphorous could even more perturb the zeolite phosphatation. This often leads to non-selective catalysts due to poor reproducibility and binder pore plugging. The method of the present invention provides a solution to selectively phosphatize zeolite overcoming the side effects of binder, metal salts or clays presence. Thus, the invention discloses that the preparation of the catalyst requires the phosphatation of zeolite before introducing any other components such as binder, metals, clays and shaping additives. This method insures the reproducibility of the preparation, the hydrothermal stability and the good catalyst performance.

BRIEF DESCRIPTION OF THE INVENTION

The present invention relates to the use of a catalyst in a MTO process to convert an alcohol or an ether into light olefins wherein said catalyst comprises a phosphorus modified zeolite and is made by a method comprising the following steps in this order,
a) the essential portion of the phosphorus is introduced into a zeolite comprising at least one ten members ring in the structure,
b) the phosphorus modified zeolite of step a) is mixed with at least a component selected among one or more binders, salts of alkali-earth metals, salts of rare-earth metals, clays and shaping additives,
b)* making a catalyst body from mixture b),
c) an optional drying step or an optional drying step followed by a washing step,
d) a calcination step,
d*) an optional washing step followed by drying,
e) optionally a small portion of phosphorus is introduced in the course of step b) or b)* or at end of step b) or b)*.

Advantageously the zeolite (or molecular sieve) contains less that 1000 wppm of sodium, less that 1000 wppm of potassium and less that 1000 wppm of iron.

Advantageously the zeolite contains less than 200 ppm of alkali and alkali-earth metals.

Advantageously the bulk Si/Al ratio of initial zeolite is below 20. Advantageously the zeolite contains less than 100 ppm of red-ox and noble elements such as Zn, Cr, Ti, Rh, Mn, Ni, V, Mo, Co, Cu, Cd, Pt, Pd, Ir, Ru, Re.

The phosphorus source is advantageously substantially free of metal compounds. It is advantageously selected among H3PO4, ammonium phosphates or organic P-compounds.

In an embodiment the phosphorus of step e) can be introduced as a component of the binder or of the clays.

The amount of phosphorous introduced into the zeolite at step a) can be from 0.5 to 30 wt %, but preferably from 0.5 to 9%.

Advantageously the molar P/Al ratio at step a) is higher than 1 by providing the excess of phosphatation agent.

The formulation steps b) and c) can be performed by means of spray—drying, extrusion, oil drop etc.

In accordance with the present invention, at the step c) and d*) the catalyst is treated with water for a period of time advantageously from 0.5 to 48 hours, preferably for a period of time from about 1 to 36 hours and most preferably from about 2 to 24 hours. The water is at a temperature between about 10° and 180° C., preferably between about 15° and 100° C. and most preferably between about 20° and 60° C. Following the water treatment, the catalyst is dried at about 60-350° C. Optionally, the water can contain ammonium or/and at least one of the ions selected from the group consisting of Li, Ag, Mg, Ca, Sr, Ba, Ce, Al, La, and mixtures thereof.

At end of step a) it is not mandatory to separate the P-zeolite from the reaction medium, the binders, salts of alkali-earth metals, salts of rare-earth metals, clays and shaping additives can be added directly into the reaction medium.

In a preferred embodiment, a low sodium content binder and clays are used.

Before the phosphatation of step a) the zeolite can be subjected to various treatments including, ion exchange, steaming, acid treatment, surface passivating by silica deposition etc.

In a preferred embodiment the sodium content in the binder and the clays is less that 5000 ppm of sodium.

Preferred zeolite structures are selected from the MFI, MTT, FER, MEL, TON, MWW, EUO, MFS, ZSM-48.

DETAILED DESCRIPTION OF THE INVENTION

As regards the MTO process to convert an alcohol or an ether into light olefins, this process has been described in many patent applications. One can cite WO 2004/016572, WO 2005/016856, WO 2008/110526, WO 2008/110528, WO 2008/110530, WO 2009/016153, WO 2009/156434 and WO 2009/016154, the content of which is incorporated in the present application.

As regards the zeolite containing at least one 10 members ring into the structure, one can cite the crystalline silicates. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, oxygen and optionally boron.

The three-letter designations "MFI" and "MEL" each representing a particular crystalline silicate structure type as established by the Structure Commission of the International Zeolite Association. Examples of a crystalline silicate of the MFI type are the synthetic zeolite ZSM-5 and silicalite and other MFI type crystalline silicates known in the art. Examples of a crystalline silicate of the MEL family are the zeolite ZSM-11 and other MEL type crystalline silicates known in the art. Other examples are Boralite D and silicalite-2 as described by the International Zeolite Association (Atlas of zeolite structure types, 1987, Butterworths). The preferred crystalline silicates have pores or channels defined by ten oxygen rings.

Crystalline silicates are microporous crystalline inorganic polymers based on a framework of $XO_4$ tetrahedra linked to each other by sharing of oxygen ions, where X may be trivalent (e.g. Al, B, ...) or tetravalent (e.g. Ge, Si, ...). The crystal structure of a crystalline silicate is defined by the specific order in which a network of tetrahedral units are linked together. The size of the crystalline silicate pore openings is determined by the number of tetrahedral units, or, alternatively, oxygen atoms, required to form the pores and the nature of the cations that are present in the pores. They possess a unique combination of the following properties: high internal surface area; uniform pores with one or more discrete sizes; ion exchangeability; good thermal stability; and ability to adsorb organic compounds. Since the pores of these crystalline silicates are similar in size to many organic molecules of practical interest, they control the ingress and egress of reactants and products, resulting in particular selectivity in catalytic reactions. Crystalline silicates with the MFI structure possess a bidirectional intersecting pore system with the following pore diameters: a straight channel along [010]: 0.53-0.56 nm and a sinusoidal channel along [100]:0.51-0.55 nm. Crystalline silicates with the MEL structure possess a bidirectional intersecting straight pore system with straight channels along [100] having pore diameters of 0.53-0.54 nm.

In a specific embodiment the crystalline silicate is steamed to remove aluminium from the crystalline silicate framework before phosphatation. The steam treatment is conducted at elevated temperature, preferably in the range of from 425 to 870° C., more preferably in the range of from 540 to 815° C. and at pressure 1-5 bara and at a water partial pressure of from 13 to 200 kPa. Preferably, the steam treatment is conducted in an atmosphere comprising from 5 to 100% steam. The steam atmosphere preferably contains from 5 to 100 vol % steam with from 0 to 95 vol % of an inert gas, preferably nitrogen. A more preferred atmosphere comprises 72 vol % steam and 28 vol % nitrogen i.e. 72 kPa steam at a pressure of one atmosphere. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

Additionally, if during the preparation of the zeolite to be phosphatized alkaline or alkaline earth metals have been used, the molecular sieve might be subjected to an ion-exchange step. Conventionally, ion-exchange is done in aqueous solutions using ammonium salts or inorganic acids.

As regards the introduction of P into the zeolite, by way of example said P-modified zeolite is made by a process comprising in that order:
    introducing P;
    separation of the solid from the liquid if any;
    an optional washing step or an optional drying step or an optional drying step followed by a washing step;
    a calcination step;

Optionally, the contact with the phosphorus-containing compound is conducted at a temperature from 40° C. to 110°. P can be introduced by any means or, by way of example, according to the recipe described in U.S. Pat. No. 3,911,041.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

According to a specific embodiment the phosphorous modified zeolite is made by a process comprising in that order:
    selecting a zeolite;
    steaming at a temperature ranging from 400 to 870° C. for 0.01-200 h;
    optional leaching with an aqueous acid solution at conditions effective to remove a substantial part of Al from the zeolite;
    introducing P with an aqueous solution containing the source of P at conditions effective to introduce advantageously at least 0.05 wt % of P;
    separation of the solid from the liquid;
    an optional washing step or an optional drying step or an optional drying step followed by a washing step;
    an optional calcination step.

In the steam treatment step, the temperature is preferably from 420 to 870° C., more preferably from 480 to 760° C. The pressure is preferably atmospheric pressure and the water partial pressure may range from 13 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

As regards step b), and the binder, it is selected so as to be resistant to the temperature and other conditions employed in the processes using the catalyst. The binder is an inorganic material selected from silica, metal silicates, metal oxides such as $ZrO_2$ and/or metals, or gels including mixtures of silica and metal oxides. It is desirable to provide a catalyst having a good crush strength. This is because in commercial use, it is desirable to prevent the catalyst from breaking down into powder-like materials. Such oxide binders have been employed normally only for the purpose of improving the crush strength of the catalyst. A particularly preferred binder for the catalyst of the present invention comprises silica. The relative proportions of the finely divided crystalline silicate material and the inorganic oxide matrix of the binder can vary widely.

As regards step b)*, in addition to enhancing the catalyst strength properties, the matrix material allows the molecular sieve crystallite powder to be bound into larger particle sizes suitable for commercial catalytic processes. The formulation of the mixture b) may be formed into a wide variety of shapes including extrudates, spheres, pills, and the like. The binder material is often, to some extent, porous in nature and may or may not be effective to promote the desired conversion of methanol to light olefins. The matrix material may also promote conversion of the feed stream and often provides reduced selectivity to the desired product or products relative to the catalyst.

Types of silica sols used to form a bound catalyst for use in the MTO process are commercially available as aquasols or organosols containing dispersed colloidal silica particles. For example, sodium silicate can be used as a silica sol. Otherwise, a silica gel, fumed or pyrogenic silica may also be used to provide a silica binder in the molecular sieve catalyst. Silicic acid is another possible source of silica. If a magnesia binder is desired, the starting slurry will contain hydrolyzed magnesium alkoxide. When a zirconia binder is used for the catalyst preparation, the preferred starting acidic sol is an aqueous zirconium acetate solution, which is preferably combined with a urea gelling agent.

As regards to the clays, It is preferred to optionally add a clay to the catalyst. The clay is usually added to the catalyst slurry before the mixing of the molecular sieve and binder, and the resultant slurry is mixed and spray dried. Clays that are used in this process to form a hardened product include, but are not limited to, kaolin, kaolinite, montmorillonite, saponite, bentonite, attapulgite and halloysite. Clays contribute to strength as a binder enhancing the attrition resistance properties of the catalyst particles, and clays in combination with binders contribute to the hardness of the particles. Clays also start as small particles and have a higher density, such that when combined with the molecular sieve and binder provide for denser particles, imparting the desirable characteristic of higher density.

As regards the salts of alkali-earth metals, salts of rare-earth metals, the metals are advantageously Ca, Mg, Sr, Ce, La or a combination thereof.

As regards the proportions of the P-zeolite, the one or more binders, salts of alkali-earth metals, salts of rare-earth metals, clays and shaping additives, advantageously the proportion of the P-zeolite is from 5 to 95 w % of the catalyst. The catalyst comprises the P-zeolite and at least a component selected among one or more binders, salts of alkali-earth metals, salts of rare-earth metals, clays and shaping additives. The amount of P-modified zeolite which is contained in the catalyst ranges more advantageously from 15 to 90 weight percent of the total catalyst, preferably 20 to 70 weight percent of the catalyst. When adding clay, the clay forms between about 10 and about 80 wt-% of the dried catalyst product. The concentration of the salts of alkali-earth metals and salts of rare-earth metals can be from 0.1 to 15 wt % of the catalyst on metal basis (Me). Advantageously the molar ratio of (Al+Me)/P in the catalyst is in the range 0.5 to 3, where the Me is alkali or rare-earth.

In mixing the P-zeolite with at least a component selected among one or more binders, salts of alkali-earth metals, salts of rare-earth metals and clays, the catalyst may be formulated into pellets, extruded into other shapes, or formed into spheres or a spray-dried powder. Typically, all the ingredients are mixed together by a mixing process. By way of example in such a process, the binder, for example silica, in the form of a gel is mixed with the P-zeolite and the resultant mixture is extruded into the desired shape, for example cylindic or multi-lobe bars. Spherical shapes can be made in rotating granulators or by oil-drop technique. Small spheres can further be made by spray-drying a catalyst suspension.

Thereafter, the catalyst is calcined in air or an inert gas, typically at a temperature of from 350 to 900° C. for a period of from 1 to 48 hours. Optionally the air or an inert gas may contain steam in concentration from 10 to 90 vol %.

As regards steps c) and d*), the dried or calcined, shaped catalyst particles may optionally be finished by contacting them with water or an aqueous exchange solution of an ionic compound. The aqueous exchange solution is characterized in that it is effective for removing undesired metallic cations that may occupy the ion exchange sites of the molecular sieve or/and introduction a desirable metallic cations. The undesirable metallic cations are Na, K, Fe, Zn, Cr, Mn, Ni, V, Mo, Co, Cu, Cd. These species can originate from inorganic template material present in the molecular sieve or, more commonly, stem from the inorganic oxide binder source material (e.g. aluminum sol). In the processing service for which the catalyst is designed (e.g. the conversion of methanol to olefins) these metal cations can promote side reactions, slow the desired reaction rate, or otherwise complicate the catalysis of the desired reaction. Some sources of the inorganic oxide binder are essentially free of undesired metal cations and therefore the dried particles produced using such sources would not necessarily require contact with an exchange solution. Water washing both before and after the finishing step may be desired to flush the catalyst of undesired solids and/or residual exchange solution.

In accordance with the present invention, at the step c) and d*) the catalyst is treated with water for a period of time advantageously from 0.5 to 48 hours, preferably for a period of time from about 1 to 36 hours and most preferably from about 2 to 24 hours. The water was at a temperature between about 10° and 180° C., preferably between about 15° and 100° C. and most preferably between about 20° and 60° C. Following the water treatment, the catalyst was dried at about 60-350° C. Optionally, the water can contain ammonium or at least one of the metallic cations ions selected from the group consisting of Li, Ag, Mg, Ca, Sr, Ba, Ce, Al, La, and mixtures thereof which do not promote side reactions and stabilize the zeolite against steam dealumination.

EXAMPLES

Example 1

A sample of zeolite ZSM-5 (Si/Al=12) in H-form (contained 445 ppm of Na, below 25 ppm of K, 178 ppm of Fe, 17 ppm of Ca & synthesized without template) was steamed 550° C. for 6 h in 100% $H_2O$ at atmospheric pressure. The sample is hereinafter identified as sample A.

Steamed solid A was subjected to a contact with 3.14M solution of $H_3PO_4$ for 4 h under reflux condition (4.2 ml/1 g pf zeolite). Then the solid was separated from the liquid phase at room temperature by filtering from the solution. Obtained material was dried at 200° C. for 16 h. The sample is hereinafter identified as sample B.

100 g of steamed solid A was subjected to a contact with 31 g of 85 wt % H3PO4 in 400 ml H2O under reflux condition for 4 h. Then the solution was cooled down and 10 g of xonotlite (calcium silicate) were added to the mixture followed by stirring at room temperature for 30 min and evaporation. The sample is hereinafter identified as sample C.

100 g of steamed solid A was subjected to a contact with 109.1 g of 85 wt % $H_3PO_4$ in 320 ml $H_2O$ under reflux condition for 4 h. Then 100 g of xonotlite (calcium silicate) were added to the mixture followed by stirring at room temperature for 30 min and evaporation. The sample is hereinafter identified as sample D.

Example 2 (Comparative)

This example illustrates the fact that the phosphated active phase is not necessary a good catalyst for conversion of oxygenates. The blending with binder and the consequence of the step given in the claims are more than a simple dilution effect.

25 g of sample B (containing 5 wt % of phosphorous) was additionally dried at 400° C. for 3 h and washed for 2 h at 80° C. with distilled water followed by filtering at room temperature (P=3.4 wt %, Al=2.7 wt %). The resulted solid was equilibrated by steaming at 600° C. for 2 h.

Catalyst tests were performed on 2 g (35-45 mesh particles) of catalyst with a essentially pure methanol feed, at $T_{in}$=550° C. and at a pressure of 0.5 barg and WHSV=1.6 $h^{-1}$, in a fixed-bed, down flow stainless-steel reactor. Prior to catalytic run all catalysts were heated in flowing $N_2$ (5 Nl/h) up to the reaction temperature. Analysis of the products has been performed on-line by a gas chromatograph equipped with a capillary column. Catalytic performance of catalyst in Table 1 is given on carbon, dry basis and coke free basis.

TABLE 1

| MeOH conversion to HC | 6.64 |
|---|---|
| C1 | 6.28 |
| DME as CH2 | 55.00 |
| CH3OH as CH2 | 38.36 |
| Ethylene | 0.11 |
| Propylene | 0.11 |
| C4 olefins | 0.10 |
| C5 olefins | 0.02 |

Example 3 (Working Example)

320 g of sample B was blended with 400 g of specific binder (P=16.7 wt %, Si=14.5, Mg=0.19, Al=0.018 wt %, K=230 ppm, Na=230 ppm, Ca=20.3 wt %), 165 ml $H_2O$, 235 ml of low sodium silica sol containing 34 wt % of $SiO_2$, and 2-3 wt % extrusion additives. The mixture was agitated for 30 min and extruded.

The specific binder was produced by blending of the equivalent mass of $NH_4H_2PO4$ and of the xonotlite in aqueous medium at room temperature (1 g of solid/4 ml of water). Afterward the stirring during 60 min the phosphated xonotlite was separated from the liquid by filtering and dried. The dried product was used as the extrusion component.

The extruded solid was dried 24 h at room temperature, then 16 h at elevated temperature followed by washing and steaming at 600° C. for 2 h. The sample hereinafter identified as E.

Catalyst tests were performed on 2 g (35-45 mesh particles) of catalyst with a essentially pure methanol feed, at $T_{in}$=550° C. and at a pressure of 0.5 barg and WHSV=1.6 $h^{-1}$, in a fixed-bed, down flow stainless-steel reactor. Prior to catalytic run all catalysts were heated in flowing $N_2$ (5 Nl/h) up to the reaction temperature. Analysis of the products has been performed on-line by a gas chromatograph equipped with a capillary column. Catalytic performance of catalyst in Table 1 is given on carbon, dry basis and coke free basis. The results are given for the average catalyst performance during 8 hours on-stream.

TABLE 2

| WHSV, $h^{-1}$ | 1.6 | 4 |
|---|---|---|
| MeOH conversion, % | 100 | 100 |
| Methane | 1.6 | 1.6 |
| Paraffins (n + i + CyP) | 6.7 | 5.7 |
| Olefins (n + i + CyO) | 85.4 | 87.5 |
| Dienes (D) | 0.5 | 0.7 |
| Aromatics (A) | 7.4 | 6.1 |
| Ethylene | 13.9 | 10.0 |
| Propylene | 41.8 | 43.4 |
| Σ olefins C4-C5 | 26.4 | 30.4 |

Example 4

Comparative, Extrusion, 40 wt % Zeolite in the Catalyst 356 g of the sample A was extruded with 338.7 g of Nyacol (40 wt % SiO2 sol), 311.3 g of fumed silica (FK500), 480 ml $H_2O$ and 2-3% of extrusion additives. The extruded solid was dried 24 h at room temperature, then 16 h at 110° C. followed by calcinations at 500° C. for 10 h. The final sample contained 40 wt % of zeolite and 60 wt % of SiO2 binder. The extruded sample was subjected to ion exchange with 0.5M NH4Cl under reflux conditions for 18 h followed by washing with water, drying at 110° C. for 16 h and calcinations at 450° C. for 6 h. The shaped and exchanged sample was treated with 3.1M H3PO4 under reflux condition for 4 h (1 g/4.2 ml) followed by cooling down, filtration and drying at 110° C. for 16 h.

The phosphated sample was washed at room temperature with 0.1 M solution of calcium acetate for 2 h (1 g/4.2 ml). Then the washed sample was dried at 110° C. for 16 h and steamed in 100 wt % $H_2O$ for 2 h at 600° C.

Example 5

Comparative, Extrusion, 40 wt % Zeolite in the Catalyst

The sample from example 4 was washed one more times at room temperature with 0.1 M solution of calcium acetate for 2 h (1 g/4.2 ml). Then the washed sample was dried at 110° C. for 16 h and steamed in 100 wt % $H_2O$ for 2 h at 600° C.

The examples 4&5 illustrate the recipe when the sample was first subjected in a contact with binder followed by phosphotation.

Example 6

Working, Extrusion, 40 wt % Zeolite in the Catalyst 4 g of the sample B was washed at room temperature with 0.1 M solution of calcium acetate for 2 h (1 g/4.2 ml), filtered and dried at 110° C. for 16 h. The 4 g of dried sample were extruded with 6 g of specific binder and 2-3 wt % of extrusion additives with the zeolite/binder ratio 40/60. The binder was obtained by blending of 40 g of xonotlite with 10 g of alumina (Condea ~75 wt % $Al_2O_3$), 50 g $(NH4)H_2PO_4$ and 50 ml $H_2O$ at 60° C. followed by filtering and drying at 110° C. for 16 h. The sodium content in the specific binder was 200 ppm.

The extruded solid was dried at 110° C. for 16 h followed by calcinations at 600° C. for 10 h.

This example shows a use of pre-phosphated sample for making a formulated catalyst by means of extrusion with a low sodium binder.

Example 7

Working, Spray-Drying 356 g of the sample A was subjected to a contact with 288 g of 85 wt % $H3PO4+972$ ml $H_2O$ at reflux condition for 4 h. Then the mixture was cooled down to room temperature and 336 g of low sodium alumina sol (20 wt % of alumina) was added. The resulted solution was keeping under stirring for 30 min followed by slow addition of NH4OH up to the resulted pH of the solution about 6.5. Then the mixture was left for maturation for at least 1 h followed by addition of 48 g of kaolin and 720 g of low sodium silica sol (34 wt % $SiO_2$, 200 ppm Na). The final pH of the slurry was about ~6. The resulted slurry was kept under stirring for at least 30 min and spray-dried. The spray-dried sample was washed with water, dried and calcined at 700° C. for 2 h.

Example 8

Working, Spray-Drying 150 g of the sample B was subjected to a contact with 630 ml of aqueous solution containing 1.5 g of dispersed xonotlite followed by addition of 450 g of low sodium silica sol (34 wt % $SiO_2$ in water, 200 ppm Na). Then the solution was stirred for one hour and spray-dried. The spray-dried solid was washed with water at room temperature for 2 h followed by filtering, drying at 110° C. for 16 h and calcinations at 700° C.

Example 9

Working, Spray-Drying 100 g of the sample C was subjected to a contact with 420 ml of aqueous solution containing 1 g of dispersed xonotlite followed by addition of 300 g of low sodium silica sol (34 wt % $SiO_2$ in water, 200 ppm Na). Then the solution was stirred for one hour and spray-dried. The spray-dried solid was washed with water at room temperature for 2 h followed by filtering, drying at 110° C. for 16 h and calcinations at 700° C.

Example 10

Working, Spray-Drying 100 g of the sample D was subjected to a contact with 420 ml of aqueous solution containing 1 g of dispersed xonotlite followed by addition of 150 g of low sodium silica sol (34 wt % $SiO_2$ in water, 200 ppm Na). Then the solution was stirred for one hour and spray-dried. The spray-dried solid was washed with water at room temperature for 2 h followed by filtering, drying at 110° C. for 16 h and calcinations at 700° C.

Example 11

Working, Spray-Drying 100 g of the sample A was subjected to a contact with 25 g of 85 wt % H3PO4 at reflux condition for 4 h followed by cooling down and addition of 120 ml of aqueous solution containing 7 g of dispersed xonotlite. The resulted slurry was kept under stirring for approximately 1 h followed by addition of 300 g of low sodium silica sol (34 wt % $SiO_2$ in water, 200 ppm Na). Then the solution was stirred for one hour and spray-dried. The spray-dried solid was dried at 200° C. for 16 h and washed with water at room temperature for 2 h followed by filtering, drying and calcinations at 700° C. for 2 h.

Example 12

MTO Performance

Catalyst tests were performed on 2 g (35-45 mesh particles) of catalyst with a essentially pure methanol feed, at $T_{in}=550°$ C. and at a pressure of 0.5 barg and WHSV=1.6 $h^{-1}$, in a fixed-bed, down flow stainless-steel reactor. Prior to catalytic run all catalysts were heated in flowing $N_2$ (5 Nl/h) up to the reaction temperature. Analysis of the products has been performed on-line by a gas chromatograph equipped with a capillary column. Catalytic performance of catalyst in Table 1 is given on carbon, dry basis and coke free basis. The results are given for the average catalyst performance during first 4 hours on-stream.

TABLE 3

| | Example | | | | | | | |
|---|---|---|---|---|---|---|---|---|
| | 4 | 5 | 6 | 7 | 8 | 9 | 10 | 11 |
| | Comp | | | Invention | | | | |
| MeOH conv, % | 98 | 100 | 100 | 100 | 100 | 100 | 100 | 100 |
| Paraffins | 8.8 | 12.7 | 6.5 | 6.2 | 8.2 | 7.6 | 6.8 | 8.2 |
| Aromatics | 10.7 | 12.9 | 10.5 | 4.5 | 6.4 | 6.5 | 5.8 | 8.0 |
| C2═+C3═ | 41.5 | 49.9 | 54.7 | 55.0 | 54.5 | 52.0 | 51.6 | 51.3 |
| Ethylene | 6.1 | 20.3 | 14.6 | 11.2 | 14.5 | 12.4 | 10.4 | 12.1 |
| Propylene | 35.4 | 29.6 | 40.1 | 43.8 | 40.0 | 39.6 | 41.2 | 39.2 |

The data illustrate higher yield of propylene obtained on the catalyst prepared in accordance with the invention.

What is claimed:
1. A process comprising:
 converting an alcohol or an ether into light olefins in the presence of a catalyst,
 wherein the catalyst comprises a phosphorous modified zeolite, wherein the process for making the catalyst comprises the following in sequential order:
 a) introducing phosphorus into a zeolite comprising at least one ten membered ring in a structure thereof to form the phosphorous modified zeolite, wherein an amount of phosphorous introduced into the zeolite ranges from 0.5 to 30 weight percent;

b) mixing the phosphorous modified zeolite of step a) with a component selected from a group consisting of binder, salt of alkali-earth metal, salt of rare-earth metal, clay, and combinations thereof, to form a mixture;

b*) making a catalyst body from the mixture of step b) by spray-drying the mixture;

c) optionally drying the catalyst body, optionally followed by washing the catalyst body;

d) calcining the catalyst body; and d*) optionally washing the calcined catalyst body, optionally followed by drying the calcined catalyst body; and wherein all the phosphorus is introduced in step (a).

2. The process of claim 1, wherein the amount of the phosphorous introduced into the zeolite at step a) ranges from 0.5 to 9 weight percent.

3. The process of claim 1, wherein the zeolite contains less than 1000 wppm of sodium, less than 1000 wppm of potassium, and less than 1000 wppm of iron.

4. The process of claim 1, wherein the zeolite contains less than 100 ppm of red-ox and noble elements.

5. The process of claim 1, wherein the zeolite contains less than 100 ppm of Zn, Cr, Ti, Rh, Mn, Ni, V, Mo, Co, Cu, Cd, Pt, Pd, Ir, Ru and Re.

6. The process of claim 1, wherein the catalyst comprises the salt of alkali-earth metal, the salt of rare-earth metal, or combinations thereof.

7. The process of claim 1, wherein the catalyst comprise Ca, Mg, Sr, Ce, La, or combinations thereof.

8. The process of claim 1, wherein the zeolite is an MFI, MTT, FER, MEL, TON, MWW, EUO, MFS, or ZSM-48.

9. The process of claim 1, wherein the catalyst comprises from 15 to 90 weight percent of the phosphorous modified zeolite, based on a total weight of the catalyst.

10. The process of claim 1, wherein the catalyst comprises from 0.1 to 15 weight percent, on metal basis (Me), of the salt of alkali-earth metal, the salt of rare-earth metal, or combinations thereof, based on a total weight of the catalyst, wherein Me is an alkali metal or a rare-earth metal.

11. The process of claim 1, wherein a molar ratio, (Al+Me)/P, in the catalyst ranges from 0.5 to 3, wherein Al is aluminum, Me is an alkali metal or a rare-earth metal, and P is phosphorous.

12. The process of claim 1, wherein the process comprises converting the alcohol into the light olefins in the presence of the catalyst.

13. The process of claim 12, wherein the alcohol is methanol, and wherein the light olefins comprise propylene and ethylene.

14. The process of claim 1, wherein the process comprises converting the ether into the light olefins in the presence of the catalyst.

15. The process of claim 1, wherein a P/Al ratio in step a) is higher than 1, and wherein P is phosphorus and Al is aluminum.

16. The process of claim 1, wherein the washing in step c) and step d*) are performed and comprise treating the catalyst with water for a period of time ranging from 0.5 to 48 hours, wherein the water is at a temperature between about 10° C. and 180° C., and wherein the drying in step c) and step d*) are performed and comprise drying the catalyst at a temperature of about 60° C. to 350° C.

17. The process of claim 16, wherein the water contains:
ammonium;
at least one ion selected from a group consisting of Li, Ag, Mg, Ca, Sr, Ba, Ce, Al, La, and mixtures thereof; or
combinations thereof.

18. The process of claim 1, wherein the mixture is a catalyst suspension.

19. A process comprising:
converting an alcohol or an ether into light olefins in the presence of a catalyst,
wherein the catalyst comprises a phosphorous modified zeolite, wherein the process for making the catalyst comprises the following in sequential order:

a) introducing phosphorus into a zeolite comprises at least one ten membered ring in a structure thereof to form the phosphorous modified zeolite;

b) mixing the phosphorous modified zeolite with a binder, a salt of an alkali-earth metal, a salt of a rare-earth metal, a clay, or combinations thereof, to form a mixture;

c) making a catalyst body from the mixture by spray-drying the mixture; and d) calcining the catalyst body; and wherein all the phosphorus is introduced in step (a).

20. The process of claim 19, wherein the process comprises converting the alcohol into light olefins in the presence of the catalyst, and wherein:
the alcohol is methanol and the light olefins comprise ethylene and propylene.

21. The process of claim 19, wherein the all phosphorus in the zeolite is introduced prior to introduction of any binder to the zeolite.

22. The process of claim 19, wherein the all phosphorus in the zeolite is introduced prior to introduction of any salt of alkali-earth metals to the zeolite.

23. The process of claim 19, wherein the all phosphorus in the zeolite is introduced prior to introduction of any salt of rare-earth metals to the zeolite.

24. The process of claim 19, wherein the all phosphorus in the zeolite is introduced prior to introduction of any clay to the zeolite.

* * * * *